US00PP28060P2

(12) United States Plant Patent
Haltermann

(10) Patent No.: US PP28,060 P2
(45) Date of Patent: May 30, 2017

(54) ***DIERVILLA* PLANT NAMED 'EL MADRIGAL'**

(50) Latin Name: *Diervilla×splendens*
Varietal Denomination: El Madrigal

(71) Applicant: Thiemo Haltermann, Barmstedt (DE)

(72) Inventor: Thiemo Haltermann, Barmstedt (DE)

(73) Assignee: SPILKERS JUNGPFLANZENOHG, Barmstedt (DE)

( * ) Notice: Subject to any disclaimer, the term of this patent is extended or adjusted under 35 U.S.C. 154(b) by 13 days.

(21) Appl. No.: 14/757,136

(22) Filed: Nov. 24, 2015

(51) Int. Cl.
*A01H 5/00* (2006.01)

(52) U.S. Cl.
USPC ..... Plt./226

(58) Field of Classification Search
USPC ..... Plt./226
See application file for complete search history.

(56) References Cited

PUBLICATIONS

UPOV-PLUTO Plant Variety Database:International Union for the Protection of New Varieties of Plants; Feb. 1, 2017, citation for 'El Madrigal' (1 page total).*

* cited by examiner

*Primary Examiner* — Susan McCormick Ewoldt
(74) *Attorney, Agent, or Firm* — Penny J. Aguirre

(57) ABSTRACT

A new cultivar of *Diervilla×splendens*, 'El Madrigal', characterized by its greenish brown foliage, its floriferous habit, and its yellow flowers.

2 Drawing Sheets

Botanical classification: *Diervilla×splendens*.
Variety denomination: 'El Madrigal'.

CROSS REFERENCE TO A RELATED APPLICATION

This application is related to a European plant breeders' rights application filed on Oct. 9, 2014, application No. 20142440. There have been no offers for sale anywhere in the world prior to the filing of this Application and no accessibility to one of ordinary skill in the art could have been derived from printed plant breeder's rights documents.

BACKGROUND OF THE INVENTION

The present invention relates to a new and distinct cultivar of *Diervilla×splendens* and will be referred to hereafter by its cultivar name, 'El Madrigal'. 'El Madrigal' is a new cultivar of bush honeysuckle grown for use as a landscape plant.

The new cultivar was discovered by the Inventor in Barmstedt, Germany as a naturally occurring branch mutation of an unnamed and unpatented plant of *Diervilla×splendens* that was growing in a container at his nursery.

Asexual reproduction of the new cultivar was first accomplished by the Inventor using softwood stem cuttings in July of 2006 in Barmstedt, Germany. Asexual propagation by softwood cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'El Madrigal' as a unique cultivar of *Diervilla*.

1. 'El Madrigal' exhibits dark greenish brown foliage.
2. 'El Madrigal' exhibits a floriferous habit.
3. 'El Madrigal' exhibits yellow flowers.

The female parent of 'El Madrigal', differs from 'El Madrigal' in having olive green foliage. 'El Madrigal' can be most closely compared to *Diervilla* cultivars 'Dise' (not patented) and 'Butterfly' (not patented). Both are similar to 'El Madrigal' in plant habit and in having yellow flowers. 'Dise' differs from 'El Madrigal' in having foliage that is medium green in color. 'Butterfly' differs from 'El Madrigal' in having foliage that is dark green in color.

BRIEF DESCRIPTION OF THE DRAWINGS

The accompanying colored photographs illustrate the overall appearance and distinct characteristics of a 2.5 year-old plant of the new cultivar as grown outdoors in a 29-cm containers in Stroe, The Netherlands.

The photograph in FIG. 1 provides a side view of 'El Madrigal' in bloom.

Figure 1:
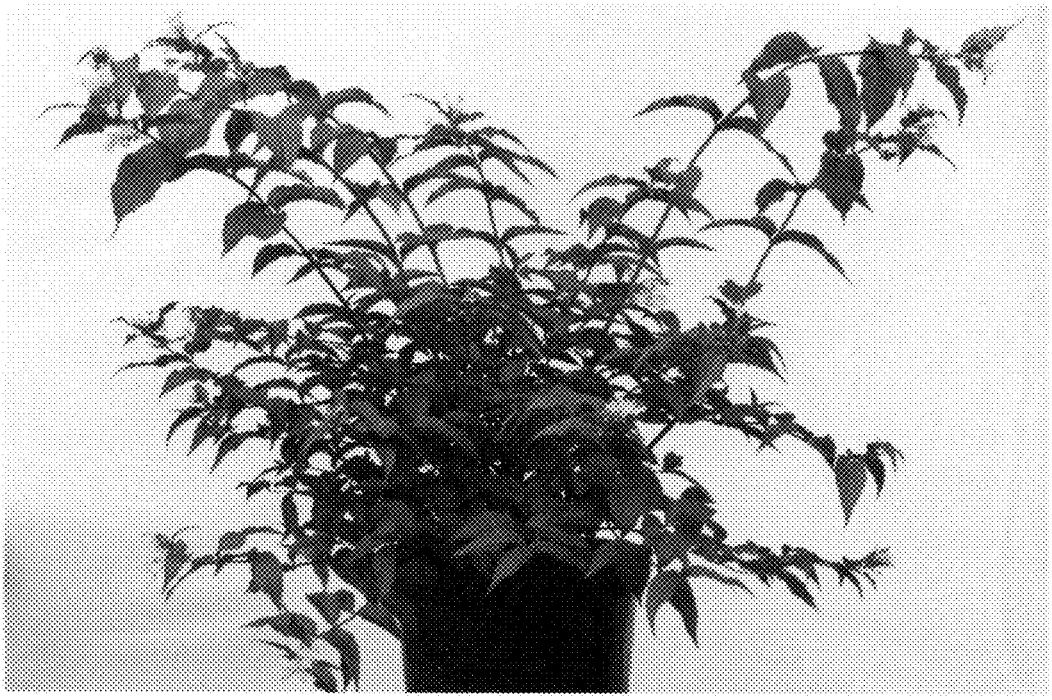
Figure 2:
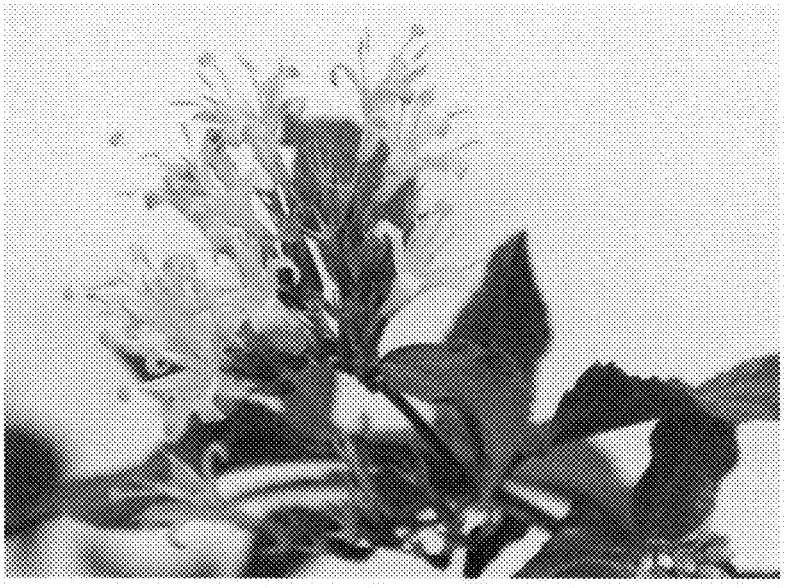

The photograph in FIG. 2 is a close-up view of an inflorescence of 'El Madrigal'.

Figure 3:
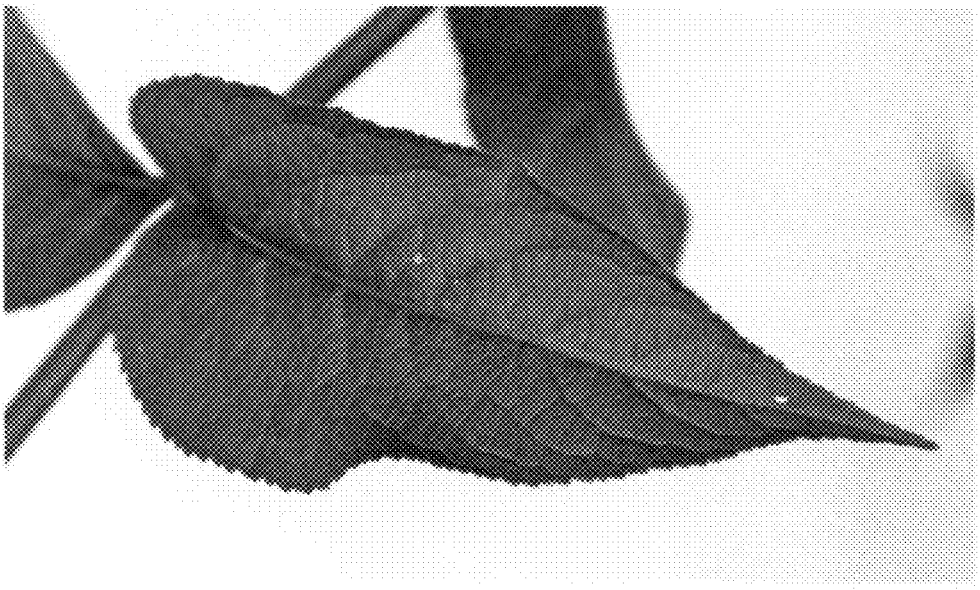

The photograph in FIG. 3. is a close-up view of a leaf of 'El Madrigal'.

The colors in the photographs are as close as possible with the digital photography techniques available, the color values cited in the detailed botanical description accurately describe the colors of the new *Diervilla*.

DETAILED BOTANICAL DESCRIPTION

The following is a detailed description of 2.5 year-old plants of the new cultivar as grown outdoors in 29-cm containers in Stroe, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms for 6 weeks from late spring into midsummer in Barmstedt, Germany.

*Plant habit.*—Upright, broad spreading.

*Plant type.*—Perennial, deciduous shrub.

*Height and spread.*—Average of 65 cm in height and 100 cm in width.

*Hardiness.*—At least in U.S.D.A. Zones 4 to 9.

*Diseases.*—No susceptability or resistance to diseases has been observed.

*Propagation.*—Softwood stem cuttings.

*Root description.*—Fibrous (no stolons were observed to date).

*Root development.*—Roots develop in 10 to 14 days in summer under greenhouse conditions on a mist bench without supplemental lighting, plants develop as a finished plant from a rooted cutting in about 12 months in a 13-cm container or larger.

*Growth rate.*—Moderate.

Stem description:

*Shape.*—Angled with four ribs.

*Stem color.*—Young stems; N186C, mature stems; between 199B to N199A.

*Stem size.*—Basal branches; average of 70 cm in length, 4 mm in diameter, lateral branches; average of 35.5 cm in length and 3 mm in diameter.

*Stem surface.*—Very slightly glossy, 2 of the 4 ribs are densely covered with very short hairs; average of 0.1 mm in length and too small to measure color.

*Stem aspect.*—Slightly drooping, held at angles between 30° and 40° (0°=upright).

*Stem strength.*—Very strong.

*Internode length.*—Basal branches; 7.6 cm in length, lateral branches 3.6 cm in length.

*Branching.*—Freely branching, average of 56 lateral branches.

Foliage description:

*Leaf shape.*—Ovate to narrow ovate.

*Leaf division.*—Simple.

*Leaf base.*—Obtuse.

*Leaf apex.*—Narrow apiculate.

*Leaf venation.*—Pinnate, color on upper surface N186C, color on lower surface; 185A.

*Leaf margins.*—Entire.

*Leaf arrangement.*—Opposite.

*Leaf attachment.*—Sessile.

*Leaf surface.*—Both surfaces are glossy and glabrous, main vein on upper surface densely covered with very short hairs; average length 0.1 mm in length and too small to measure color.

*Leaf size.*—Average of 9.2 cm in length and 4.2 cm in width.

*Leaf quantity.*—Average of 20 leaves (10 pairs) per branch.

*Leaf color.*—Young upper surface; color between 200B and 200C, young lower surface; color between 177A and 200C, mature upper surface; color between 200B and 200C with a sheen of 152A, mature lower surface; color between 148A and N199A.

*Petioles.*—Average of 4 mm in length and 2 mm in width, upper and lower surface 187B in color.

*Stipules.*—Not present.

Inflorescence description:

*Inflorescence type.*—Terminal and axillary compound cymes of tubular flowers.

*Inflorescence size.*—Average of 4.3 cm in height and 5.3 cm in width.

*Flower fragrance.*—None.

*Lastingness of inflorescence.*—Average of one week, self-cleaning.

*Flower quantity.*—Average of 20 flowers per terminal cymes and an average of 8 flowers per axillary cymes, about 800 per plant.

*Flower type.*—Single, campanulate.

*Flower size.*—Average of 2.6 cm in depth and 1.4 cm in diameter.

*Flower aspect.*—Outward.

*Flower buds.*—Narrow oblong in shape, color between 150A and 151D with base 177A, average of 1.5 cm in length and 3 mm in diamteter, surface is waxy.

*Peduncles.*—About 1.5 cm in length and 1 mm in diameter, strong, N186C in color, surface texture glabrous, held straight on top of the lateral branch.

*Pedicels.*—Up to 3.5 mm in length and 0.5 mm in diameter, moderately strong, color is N199B and tinged with 147B, held at an average angle of 20° to peduncle (=0°) glabrous surface.

*Calyx.*—Rotate in shape, average of 3 mm in length and 2.5 mm in diameter, surface texture glabrous.

*Sepals.*—5, narrow lanceolate in shape, narrow acuminate apex, base fused and broad cuneate, smooth and dull surface, entire margin, average of 3 mm in length and 3 mm in width, color: immature and mature, upper and lower surface; 145B and tinged with 175D near apex.

*Petals.*—5, lower 65% fused into tube, both surfaces of lobes and tube are matte and glabrous with one lower lobe having sparse short hairs; an average of 0.5 mm in length and NN155D in color, lobes are narrow oblong in shape, entire margin, broad acute apex, average of 2 cm in length and 3 mm in width, tube is an average of 1.5 cm in length and 7 mm in width, color: upper surface when opening; 154C with lower lobe 2A, lower surface when opening; 1A, upper surface when fully open; color between 1A and 2B with lower lobe 5A, lower surface when fully open; color between 1A and 2B with lower lobe 5A, color of all surfaces fade to 34C.

Reproductive organs:

*Gynoecium.*—Pistil; 1, average of 2.1 cm in length, style; 2 cm in length, N144A in color, stigma; club-shaped, average of 2 mm in diameter, 145D in color, ovary; oblong in shape, N186C to 200B in color, up to 5 mm in depth and 1.5 mm in diameter.

*Androcoecium.*—Stamens; 5, filaments; 1B to 1C in color, 1.3 cm in length, anthers; 3 mm in length, 8B in color, dorsifixed, narrow oblong in shape, pollen is moderate, 160C in color.

*Fruit and seed.*—No fruit or seed has been observed to date.

It is claimed:

1. A new and distinct cultivar of *Diervilla* plant named 'El Madrigal' as herein illustrated and described.

* * * * *